United States Patent [19]

Cassinelli et al.

[11] 4,421,851

[45] Dec. 20, 1983

[54] ANTITUMOR ANTIBIOTICS

[75] Inventors: Giuseppe Cassinelli, Pavia; Arpad Grein, Milan; Sergio Merli, Milan; Giovanni Rivola, Milan, all of Italy

[73] Assignee: Farmitalia Carlo Erba S.p.A., Milan, Italy

[21] Appl. No.: 321,558

[22] Filed: Nov. 16, 1981

Related U.S. Application Data

[62] Division of Ser. No. 94,671, Nov. 15, 1979, Pat. No. 4,370,474.

[30] Foreign Application Priority Data

Nov. 21, 1978 [GB] United Kingdom ............... 45434/78

[51] Int. Cl.$^3$ ..................... C12P 19/56; C12N 1/14; C12R 1/465
[52] U.S. Cl. ..................... 435/78; 260/365; 424/181; 435/253; 435/886; 536/6.4
[58] Field of Search ................. 536/6.4; 260/365; 424/181; 435/78, 253, 886

[56] References Cited

U.S. PATENT DOCUMENTS

| | | | |
|---|---|---|---|
| 3,590,028 | 6/1971 | Arcamone et al. | 435/78 |
| 4,247,545 | 1/1981 | Cassinelli et al. | 424/181 |
| 4,263,428 | 4/1981 | Apple et al. | 536/6.4 |
| 4,309,503 | 1/1982 | Cassinelli et al. | 435/78 |

FOREIGN PATENT DOCUMENTS 26849  4/1981  European Pat. Off. ............. 435/78

*Primary Examiner*—Robert J. Warden
*Attorney, Agent, or Firm*—Hubbell, Cohen, Stiefel & Gross

[57] ABSTRACT

Anthracycline glycosides W, X, Y and Z which are prepared by the fermentation of mutant F.I. 416 of *Streptomyces peucetius* var. *caesius*. The new compounds are useful against both gram positive and gram negative bacteria and as antitumor agents.

6 Claims, No Drawings

ANTITUMOR ANTIBIOTICS

This is a division of application Ser. No. 094,671, filed Nov. 15, 1979 now U.S. Pat. No. 4,370,474.

BACKGROUND OF THE INVENTION

1. Field of the Invention

The present invention relates to new anthracycline antibiotics, a new microorganism which is a mutant of the strain *Streptomyces peucetius* var. *caesius*, for producing these new compounds and a process for making these compounds. These compounds possess antitumor activity and antibacterial activity against both gram negative and gram positive bacteria.

2. The Prior Art

DAUNOMYCIN and ADRIAMYCIN, which are trademarks of the unrecorded assignee of this application for daunorubicin and doxorubicin, respectively, are known as useful in treating certain mammalian tumors. The aerobic fermentation of the microorganism *Streptomyces peucetius* var. *caesius* to produce ADRIAMYCIN is also known. See U.S. Pat. No. 3,590,028.

SUMMARY OF THE INVENTION

The invention relates to new anthracycline antibiotics, to the production of these antibiotics by fermentation, to methods for the recovery and concentration of these antibiotics from crude solutions, to processes for the purification of the antibiotics and to the preparation of their salts as well as to a new microorganism useful in preparation of these compounds.

The invention includes within its scope the new antibiotics in diluted form, as crude concentrates and in pure crystalline forms. These novel anthracyclines are active as antitumor agents and also as antibacterial agents. The effects of the new antibiotics, together with their chemical and physical properties, differentiate them from previously described antibiotics.

The new antibiotics, designated herein as antibiotics W, X, Y and Z, are formed during the fermentation of a mutant strain of *Streptomyces peucetius* var. *caesius*.

The microorganism used in the process of this invention is obtained by a mutagenic treatment with N-methyl-N'-nitro-N-nitrosoguanidine of *Streptomyces peucetius* var. *caesius* (Arcamone et al, Biotechnol. Bioengeen., XI, 1969, 1101–1110). The new strain thus obtained has been given the code number 416 F.I. of the Farmitalia Collection of Microorganisms and has been deposited at the Deutsche Sammlung Mikroorganismen under the numer 1367 DSM, at the American Type Culture Collection under number 31428 ATCC and at the Fermentation Research Institute, Japan, under number 4622 F.R.I.

As in the case of many antibiotic-producing cultures, fermentation of strain 416 F.I. results in the production of a mixture of a complex of components. Four bioactive anthracycline components, herein designed ANTIBIOTICS W, X, Y and Z have been separated from the complex produced by the above-mentioned microorganism.

Antibiotics W, Y and Z have been determined to have the following structural formulae:

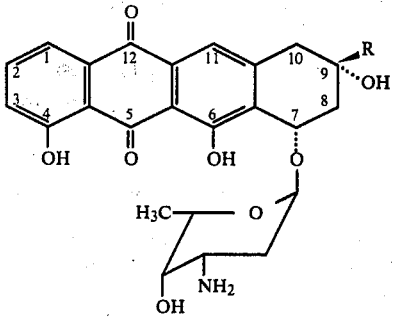

I: Antibiotic W R=—CO—CH$_2$—OH
II: Antibiotic Y R=—CO—CH$_3$
III: Antibiotic Z R=—CH$_2$—CH$_3$
respectively corresponding to:
11-DEOXY-14-HYDROXY-CARMINOMYCIN for ANTIBIOTIC W (I)
11-DEOXY-CARMINOMYCIN for ANTIBIOTIC Y (II)
11-DEOXY-13-DEOXO-CARMINOMYCIN for ANTIBIOTIC Z (III)

As shown, all the above components are anthracycline glycosides containing daunosamine (3-amino-2,3,6-trideoxy-L-lyxo-hexose), the amino sugar component of DAUNOMYCIN and ADRIAMYCIN (F. Arcamone, G. Cassinelli, P. Orezzi, G. Franceschi and R. Mondelli, J.Am.Chem.Soc., 86, 5335, 1964 and U.S. Pat. No. 3,590,028). The structure of the components were determined by analysis of their infrared, ultraviolet, visible, mass and magnetic resonance spectra and are in agreement with the chemical and physical data provided below.

The new anthracycline complex and its individual components form salts with both acids and bases and pharmaceutically acceptable salts of the complex and components are included within the scope of the present invention. Examples of such pharmaceutically acceptable salts include salts with acid such as hydrochloric, sulfuric, nitric and phosphoric and with metallic cations, e.g., alkali metal or alkaline-earth metal cations such as sodium, potassium, calcium and magnesium and also with other cations such as trivalent iron cations. Preparation of the novel anthracycline antibiotics of the present invention is described below.

DESCRIPTION OF THE PREFERRED EMBODIMENTS

The invention will now be described in greater detail in conjunction with the following characterization of the novel microorganism hereof, the process for the preparation of new anthracycline antibiotics therewith, and those antibiotics per se.

I. THE MICROORGANISM

A. Microscopic Properties of Strain 416 F.I.

The substrate mycelium is formed by fairly branched hyphae, 0.5 to 0.9$\mu$ in diameter, of variable length; the aerial mycelium which arises from the former is formed by fairly long, from straight to flexous hyphae 1.1 to 1.6$\mu$ in diameter; from these, by sympodial branching in a fasciculate fashion, spore bearing hyphae of variable length depart, ending in hooks or loops. The spores are spherical and of from about 1 to 2$\mu$ in diameter, at first disposed in chains, then free. Under the electron microscope the spores appear nearly spherical, of irregular contours, with a warty-surface.

B. Macroscopic Properties of Strain 416 F.I.

The cultural characteristics of strain 416 F.I. are given in Table 1.

Growth is generally good on organic as well as on synthetic media; observations of growth on the media cited in Table 1 have been made from the 5th day of incubation at 28° C. until the end of growth. The biochemical and physiological proerties of strain 416 F.I. are given in Table 2.

No growth is observed at a temperature above 40° C. Sclerotia formation has not been observed on the media cited in Table 1.

TABLE 1

| Cultural Characteristics Of Strain 416 F.I. | | | |
|---|---|---|---|
| Medium | Substrate mycelium | Aerial mycelium | Soluble pigments |
| Bennett's agar (Waksman 1961) | growth abundant slightly lichenoid straw to lemon yellow colored | absent | lemon-yellow |
| Czapek's agar (Waksman 1961) | good growth, flat, compact, colorless | abundant, grey | straw-yellow |
| Asparagine-glucose agar (Waksman, 1961) | growth abundant, flat, compact lemon-yellow colored | abundant, grey-blue-green | lemon-yellow to slightly green |
| Glycin-glycerol agar (Waksman, 1961) | abundant growth, raised and rigid; colonies sometimes crater-like; lemon-orange colored | absent | lemon-orange |
| Emerson's agar (Waksman, 1961) | abundant growth, raised and ridged, crater-like; honey colored | absent | yellow |
| Inorganic salts-starch agar (Pridham et al. 1957) | growth abundant, flat; straw-yellow colored | abundant, grey-green | straw-yellow |
| Potato-glucose agar (Waksman, 1961) | growth abundant, slightly raised; light orange colored | moderate, grey | lemon-ochre |
| Asparagine-glycerol agar (Waksman, 1961) | growth abundant, raised and ridged colonies crater-like lemon-yellow colored | absent | lemon-yellow |
| Yeast extract-glucose agar (Waksman 1961) | growth abundant, raised and ridged; colonies crater-like; straw-yellow colored | absent | yellow |
| Starch-casein agar (Waksman, 1961) | growth abundant flat; straw-yellow colored | grey | straw-yellow |
| SA-agar (see for composition, maintenance medium in Example 1) | growth abundant, raised and ridged; straw-yellow colored | grey with blue-green tonalities | straw-yellow |

Waksman S. A.: "The Actinomycetes" Vol. II, 1961, William Wilkins Co., Baltimore.
Pridham T. G., Anderson P., Foley C., Lindenfelser L. A., Hesseltine C. W. and Benedict R. G.: A selection of media for maintenance and taxonomic studies of Streptomyces Antibiotics Ann. 1956/1957, 947–953.

TABLE 2

| Physiological And Biochemical Properties of Strain 416 F.I.* | |
|---|---|
| Utilization of glucose | + |
| Utilization of sucrose | − |
| Utilization of D-xylose | + |
| Utilization of mannitol | − |
| Utilization of m-inositol | + |
| Utilization of L-arabinose | + |
| Utilization of D-fructose | + |
| Utilization of adonitol | − |
| Utilization of lactose | − |
| Utilization of d(+)mannose | + |
| Utilization of maltose | + |
| Utilization of raffinose | − |
| Utilization of L-rhamnose | − |
| Utilization of alpha-alpha-Trehalose | + |
| Utilization of esculin | + |
| Utilization of glycerol | + |
| Utilization of Na—citrate | + |
| Utilization of NH4—succinate | + |
| Utilization of Na—acetate | − |
| Utilization of NH4—tartrate | − |

TABLE 2-continued

| Physiological And Biochemical Properties of Strain 416 F.I.* | |
|---|---|
| Utilization of glycogen | + |
| Utilization of paraffin | − |
| Negative control | − |
| Liquefaction of gelatin | + |
| Tyrosine decomposition | + |
| Melanin formation | − |
| Hydrolysis of starch | + |
| $H_2S$ formation | + |
| Nitrate reduction | + |
| Milk (pepton- and coag.) | + |
| Antibiotics produced: new anthracyclines | |

+ = positive reaction
− = negative reaction
*The medium for the carbohydrate utilization test used is that described by R. D. Gordon and M. L. Smith: J. Bacteriology 69, 1955, pp. 147–150. The media used for the other physiological reactions are those reported by S. A. Waksman "The Actinomycetes", Vol. II, 1961, The Williams Wilkins Company, Baltimore.

C. Identification and Classification of Strain 416 F.I.

The overall characteristics shown by strain 416 F.I. clearly correspond to those given for the genus Streptomyces Waksman et Henrici. Furthermore, the morphological, cultural and physiological characteristics shown by strain 416 F.I. correspond to those described for the species Streptomyces peucetius var. caesius (U.S. Pat. No. 3,590,028; Arcamone et al., Biotechnol. Bioengeen., XI, 1969, 1101–1110), from which it nevertheless differs because of its ability to produce a yellow soluble pigment, because it utilizes m-inositol, L-arabinose and esculin, whereas it does not utilize sucrose, mannitol, and raffinose, and finally because it produces new anthracycline antibiotics.

We therefore consider strain 416 F.I. a variety of Streptomyces peucetius var. casesius, to which the designation Streptomyces peucetius var. aureus is given.

II. THE FERMENTATION PROCESS

The novel fermentation process of the present invention is carried out by the usual well known methods and comprises culturing the mutated microorganism in a previously sterilized aqueous liquid culture medium under aerobic conditions at a temperature of from 25° C to 37° C. (preferably at about 28° C.) over a period of time of from 3 to 7 days (preferably about 5 days) and at a pH which initially is from 6.5 to 7.0 and which at the end of the fermentation process is from 6.5 to 8.0. The culture medium comprises carbon and nitrogen sources as well as mineral salts.

The carbon source may, for example, be starch, dextrin, glucose, glycerin, mannite, maltose, corn steep liquor, distillers solubles, soybean oil or soybean meal. The nitrogen source may, for example, be dry yeast, meat peptone or casein, as well as such of the above carbon sources as contain nitrogen. Good results are even obtained by using ammonium salts such as ammonium nitrate, ammonium sulphates and diammonium phosphates. The mineral salts useful in the fermentation may vary according to the medium employed.

In a medium containing complex substances such as various meals and fermentation residues, the addition of calcium carbonate and sodium or potassium phosphates has proved useful. In media containing glucose, or ammonium salts, much higher levels of mineral salts of potassium, sodium or calcium are necessary, and additionally microamounts of salts of metals such as iron, zinc, copper, magnesium and manganese are needed. The addition of sulfur containing compounds such as sulfanilamide, sulfathiazole, sulfapyridazine, penthiobarbital and ethionine may also be useful.

The fermentation may be carried out in Erlenmeyer flasks or in laboratory or industrial fermenters of various capacities.

A. Analytical Methods

When samples of fermentation broths and crude preparations are subjected to paper chromatography, using Whatman No. 1 paper, buffered with M/15 phosphate buffer at pH 5.4, employing a mixture of n-propanol: ethyl acetate: water (7:1:2) as the eluant, and the paper strip is bioautographed against *Bacillus subtilis*, four major components are found to recur. These have been designated antibiotic W (Rf 0.45), antibiotic X (Rf 0.60), Y (Rf. 0.64), and Z (Bf 0.70). Two minor components also recur and these have been identified as glycosides A and C (respectively Rf 0.30 and 0.55), previously described in British patent application No. 5246/78 the disclosure of which is incorporated by this reference herein.

A quantitive estimation of the total yellow constituents present in the fermentation broths can be made by the following method. To a sample of broth, adjusted to pH 8.6, two volumes of chloroform: methanol (9:1) are added and the resulting mixture is sonicated for one minute at R.T. Then, on a sample of the organic phase, diluted with acidic methanol, the total content of the yellow anthracyclines and of their aglycones can be spectrophotometrically determined at 430 nm. On a sample of the organic phase concentrated under reduced pressure quantitative determination of the single antibiotics can be obtained by preparative TLC using the above reported system. The different yellow colored zones are scraped off and eluted with methanol. Each constituent is spectrophotometrically determined at 430 nm. The antibiotic Y is usually the major constituent in the fermentation broths.

B. Isolation Procedure

After the fermentation is completed, the active compounds are contained in the mycelia and in the fermentation liquors. These anthracycline antibiotics can be extracted at pH 8.5 to 9.0 as free bases from the culture broth "in toto" with a water immiscible organic solvent such as butanol, methyl isobutyl ketone, chloroform, methylene dichloride and ethyl acetate. Preferably, the mycelia and the fermentation liquors are separated by filtration at pH 4 with the aid of diatomaceous earth, and then extracted separately.

The filter cake is extracted with a water-soluble solvent, such as acetone or a lower alcohol, preferably with methanol.

The mycelium extracts are collected and concentrated under reduced pressure.

The concentrate is combined with the filtered broth, adjusted to pH 8.5 to 9, then extracted with a water immiscible organic solvent, preferably chloroform or n-butanol. The extracts are concentrated under reduced pressure and the anthracycline antibiotics may be precipitated by addition of a five-fold volume of n-hexane. The constituents of the crude mixture may be fractionated and purified by column chromatographic methods.

C. Purification Procedure

Further purification of the antibiotic activity and its separation into four components, namely antibiotics W, X, Y and Z, may be effected by silica gel column chromatography. The crude orange brown powder is dissolved in chloroform and the solution is chromatographed on buffered silica gel with a gradient of chloroform: methanol: water mixture. The antibiotic Z is eluted first, with a 94.8:5:0.2 mixture, followed by the antibiotic Y with a 92.2:7.5:0.3 mixture, the antibiotic X eluted with a 89.5:10:0.5 mixture and the antibiotic W eluted with a 300:55:6 mixture. The components are usually separated as shown by paper and thin layer chromatography and the antibiotics W, Y and Z are obtained as their hydrochlorides in crystalline form by addition of an equivalent of methanolic hydrogen chloride.

III. THE ANTIBIOTICS

A. Chemical And Physical Properties

The antibiotics W, X, Y and Z show some properties common to known anthracycline antibiotics, but they can be distinguished on the basis of their chemical and physical characteristics.

All the new anthracyclines have similar solubilities; as free bases they are soluble in chloroform, methylene dichloride, acetone, methanol, ethanol, aqueous alcohols, acidic water, dioxane and pyridine—on the other hand they are sparingly soluble or insoluble in diethyl ether, n-hexane, cyclohexane and petroleum ether. As hydrochlorides they are soluble in water, methanol, ethanol and aqueous alcohols, but insoluble in acetone, benzene, chloroform, diethyl ether and petroleum ether.

The new compounds can be used as indicators, being orange yellow in neutral and acidic solutions in which they also show greenish yellow flurescence under U.V. light. Their alkaline solutions are red-brown and when treated with alcoholic magnesium acetate they give orange-red solutions.

All these properties and the absorption spectra in the ultraviolet and visible regions indicate that these new compounds belong to the group of anthracycline antibiotics.

The chemical and physical properties of the three main components, namely antibiotics W, Y and Z, isolated as their hydrochlorides, are reported in Table 3 below.

The antibiotics W, X, Y and Z are glycosidic compounds formed by a tetracyclic aglycone (anthracyclinone) and an amino sugar.

For example, acid hydrolysis of the antibiotic Y with 0.2 N-hydrochloric acid for 25 minutes at 90° C. gives a water insoluble aglycone in the form of yellow orange needles, m.p. 168°; U.V. spectrum $\lambda_{max}^{MeOH}$ 227, 258, 430 nm ($E_1^{1\%}{}_{cm}$=880, 560, 263); I.R. spectrum (KBr): 3,430; 2,920; 1,710; 1,670; 1,620; 1,470; 1,450; 1,420; 1,385; 1,355; 1,285; 1,260; 1,210; 1,185; 1,160; 1,125; 1,085; 1,040; 1,015; 982; 930; 900; 885; 860; and 835 cm$^{-1}$. The aglycone of the antibiotic Y has an empirical formula corresponding to $C_{20}H_{16}O_7$; M.W. 368.33. The molecular weight was confirmed by mass spectroscopy; m/e 368 (M+); 332 (M-2 $H_2O$); 317 (M-2 $H_2O$—$CH_3$) and 289 (M-2 $H_2O$—$COCH_3$).

Acid hydrolysis of the other purified antibiotics gives three different yellow aglycones, characterized and identified according to their chromatographic behavior as indicated in Table 4 below.

The aqueous soluble fractions of the acid hydrolyses of the purified antibiotics W, X, Y and Z contain a reducing amino-sugar having the same chromatographic behavior as daunosamine (3-amino-2,3,6-trideoxyl-L-lyxohexose), the aminosugar component of Daunomycin (daunorubicin) and Adriamycin (doxorubicin).

TABLE 4

| Thin Layer Chromatography Rf values of Aglycones* | | |
|---|---|---|
| Compound | Solvent 1 | Solvent 2 |
| Aglycone of antibiotic W | Rf 0.15 | Rf 0.30 |
| Aglycone of antibiotic X | Rf 0.11 | Rf 0.20 |
| Aglycone of antibiotic Y | Rf 0.50 | Rf 0.62 |
| Aglycone of antibiotic Z | Rf 0.42 | Rf 0.56 |

*On 0.25 mm thick silica gel 60-F-254 plates (Merck): solvent 1, chloroform-acetone 4:1, and solvent 2, methylene dichloride-methanol 97:3.

B. Biological Activity Data

1. Antibacterial Activity

The in vitro minimal inhibitory concentrations (MIC's) of antibiotics W, Y and Z as hydrochlorides, determined against varying microorganisms using the standard test tube dilution procedure, are reported in Table 5 below.

TABLE 5

| Antibiotic MIC Values of Antibiotics W, Y and Z | | | |
|---|---|---|---|
| | MIC in g/ml | | |
| Test organism | Antibiotic W | Antibiotic Y | Antibiotic Z |
| Staphylococcus aureus 209 P | 25 | 25 | 100 |
| Sarcina lutea ATCC 9341 | 12.5 | 3.12 | 6.25 |
| Bacillus subtilis ATCC 6633 | 50 | 12.5 | 25 |
| Escherichia coli B | 12.5 | 6.25 | 25 |

2. Antitumor Activity

The new antibiotics W, Y and Z have been tested against HeLa cells in vitro (time of exposure to the drugs: 24 hours), and on L 1210 and P 388 leukemia in mice in comparison with daunorubicin. The results are reported in Table 6.

TABLE 3

| Chemical and Physical Properties of Antibiotics W, Y and Z | | | |
|---|---|---|---|
| Property | Antibiotic W.HCl | Antibiotic Y.HCl | Antibiotic Z.HCl |
| Melting point | 208°-210° (dec.) | 195°-196° (dec.) | 200°-201° (dec.) |
| $[\alpha]_D^{23°}$ (c 0.1 in MeOH) | +130° | +150° | +134° |
| U.V. VIS Spectra | | | |
| $\lambda_{max}^{MeOH}$ 1% | 228,258,430 nm | 228,258,430 nm | 228,258,430 nm |
| $E_{1cm}$ | 650,435,217 | 670,440,208 | 660,430,216 |
| $\lambda_{max}^{0.01\ N\ NaOH}$ 1% | 520 nm | 520 nm | 520 nm |
| $E_{1cm}$ | 152 | 150 | 150 |
| I.R. Spectra (KBr): cm$^{-1}$ | 3,700–2,600 | 1,180  3,700–2,600 | 1,162  3,650–2,500  1,158 |
| | 1,720 | 1,155  1,710 | 1,118  1,665  1,115 |
| | 1,670 | 1,115  1,667 | 1,085  1,620  1,085 |
| | 1,615 | 1,070  1,620 | 1,015  1,470  1,010 |
| | 1,470 | 1,010  1,518 | 985  1,450  985 |
| | 1,450 | 985  1,475 | 945  1,420  838 |
| | 1,415 | 970  1,420 | 840  1,385  820 |
| | 1,385 | 935  1,450 | 900  1,290  752 |
| | 1,285 | 840 | 1,215  435 |
| | 1,245 | 750  1,380 | 820 |
| | 1,215 | 440  1,230 | 780 |
| | | 1,215 | 755 |
| | | | 450 |
| Empirical Formula | $C_{26}H_{27}NO_{10}$.HCl | $C_{26}H_{27}NO_9$.HCl | $C_{26}H_{29}NO_8$.HCl |
| Molecular weight confirmed by mass spectroscopy | 564 | 548 | 534 |

TABLE 6

Antitumor Activity of Antibiotics W, Y and Z

| Compound | Effect of HeLa cells[a] viability in vitro ID$_{50}$ ng/ml | Dose mg/kg | L-1210[b] T/C % | L-1210[b] Toxic[c] deaths | P-388[b] T/C % | P-388[b] Toxic[c] deaths |
|---|---|---|---|---|---|---|
| Daunorubicin.HCl | 7.5 | 2.9 | 144–150 | | 170 | 2/8 |
| (Daunomycin) | | 4.4 | 140–162 | 1/20 | 175 | 6/8 |
| | | 6.6 | 144–162 | 3/19 | 160 | 7/8 |
| Antibiotic W.HCl | 8.8 | 1.0 | | | 159 | 0/10 |
| (IMI-103) | | 1.5 | | | 172 | 0/20 |
| | | 2.25 | | | 163 | 0/20 |
| | | 3.4 | | | 190 | 0/10 |
| | | 5.0 | | | 204 | 1/9 |
| Antibiotic Y.HCl | 9.6 | 0.8 | 111 | | | |
| (IMI-86) | | 1.2 | 128 | | 145 | |
| | | 1.9 | 122 | | 159 | |
| | | 2.9 | 111 | 8/10 | | |
| Antibiotic Z.HCl | 15.0 | 1.0 | | | 140 | |
| (IMI-87) | | 2.0 | | | 140 | |
| | | 2.9 | 125 | | | |
| | | 4.4 | 131 | 2/10 | 100 | 7/8 |
| | | 6.6 | 137 | 5/10 | | |

[a]HeLa cells were exposed to the drugs for 24 hrs, then plated.
[b]Mice were treated i.p. on day 1 after tumor cell inoculation.
[c]Evaluated on the basis of macroscopic findings.

IV. EXAMPLES

The following examples, wherein all parts are given by weight unless otherwise specified, specifically illustrate the novel microorganism, the fermentation process, and the antibiotic substances of the present invention.

EXAMPLE 1

A culture of *Streptomyces peucetius* var. *aureus* strain 416 F.I. was grown for 14 days at 28° C. on agar slants of medium SA having the following compositions; glucose, 3%; brewer's yeast, 1.2%; sodium chloride, 0.1%; monopotassium dihydrogen orthophosphate, 0.05%; calcium carbonate, 0.1%; magnesium sulfate, 0.005%; ferrous sulfate heptahydrate, 0.0005%; zinc sulfate heptahydrate, 0.0005%; copper sulfate pentahydrate, 0.0005%; agar, 2%; tap water up to 100 ml; pH 6.7. The medium was sterilized by heating in an autoclave at 115° C. for 20 minutes.

The spores of the culture so obtained were collected and suspended in 3 ml of sterile distilled water. The resulting suspension was inoculated in 300 ml Erlenmyer flasks containing 60 ml of the following liquid growth medium; brewer's dry yeast, 0.3%; peptone, 0.5%; calcium nitrate tetrahydrate, 0.05%; tap water up to 1000 ml. Sterilization was effected by heating in an autoclave at 120° C. for 20 minutes. The pH of this medium after sterilization was between 6.8 and 7.0.

The inoculated flasks were shaken for 2 days at a temperature of 28° C. on a rotary shaker running at 250 rpm and describing a circle of 7 cm in diameter. 1.5 ml of each of the cultures grown as described above were inoculated in 300 ml Erlenmeyer flasks containing 50 ml of the following production medium: glucose, 6%; brewer's dry yeast, 3%; sodium chloride, 0.2%; monopotassium dihydrogen orthophosphate, 0.1%; calcium carbonate, 0.2%; magnesium sulfate, 0.01%; ferrous sulfate heptahydrate, 0.001%; zinc sulfate heptahydrate, 0.001%; copper sulfate pentahydrate, 0.001%; tap water up to 100 ml, pH 6.7. Sterilization was effected by heating in an autoclave at 115° C. for 20 minutes. The flasks thus inoculated were incubated at 28° C. for 7 days in conditions identical to those described for the seed phase.

At the twenty-fourth hour of fermentation sulfanilamide was added to each flask at a concentration of 0.5 g/l. At the forty-eighth hour of fermentation a further addition of this substance at a concentration of 1 g/l was made to each flask.

The maximum concentration of the active compounds was reached between the sixth and seventh days of fermentation with a production of 70 mcg/ml.

EXAMPLE 2

The culture of strain 416 F.I. was obtained as described in Example 1. The spores of three slants were pooled and collected in 10 ml of sterile distilled water; the resulting suspension was inoculated in a 2 liter baffled round-bottomed flask containing 500 ml of the seed medium described in Example 1. The flask was incubated for 48 hours on a rotary shaker running at 120 rpm and describing a circle of 70 mm diameter, at a temperature of 28° C.

Thw whole seed was inoculated in an 80 liter stainless steel fermenter containing 50 liters of the production medium described in Example 1 sterilized by heating at 120° C. for 30 minutes. At the twenty-fourth hour of fermentation, sulfanilamide was added at a concentration of 0.5 g/l. At the forty-eighth hour of fermentation further sulfanilamide was added at a concentration of 1 g/l. The fermentation was carried out at 28° C., stirring at 230 rpm and aerated with an air flow of 0.7 liter/liter of the medium/minute.

The maximum concentration of the active compounds was reached between the sixth and seventh days of fermentation with a production of 50 mcg/ml.

EXAMPLE 3

Example 2 was repeated save that the additions of sulfanilamide were omitted. The maximum concentration of the active compounds was reached between the sixth and seventh days of fermentation with a production of 5 mcg/ml.

EXAMPLE 4

The whole beer (30 liters) from a fermentation carried out as described in Example 2 was adjusted to a pH of about 4 with hydrochloric acid and filtered, using 3% diatomaceous earth as a filter-aid, to yield a cake and a filtrate which were separately extracted.

The wet filter cake was extracted with about 15 liters of methanol. The extract was concentrated under reduced pressure and then combined with the filtered broth. The mixture was adjusted to a pH of about 8.5–9.0 and then extracted twice with one half volume of chloroform. The combined organic extracts were washed with water, dried on anhydrous sodium sulfate, and then concentrated under reduced pressure to a volume of about 200 ml. By addition of 1 liter of n-hexane, the crude glycosidic fraction precipitated as a yellow brown powder (1.5 g).

EXAMPLE 5

Separation of Antibiotics W, X, Y and Z

A chloroform solution of the crude glycosides as free bases (1.5 g in 30 ml), prepared as described in Example 4, was put on a column of silica gel buffered with M/15 phosphate buffer at pH 7, prepared in chloroform. The column was washed with chloroform and eluted with a gradient of chloroform-methanol-water mixture.

Using a 92.2:2:3.5:0.2 mixture some yellow colored aglycones were eluted followed by the antibiotic Z. Elution with a 92.2:7.5:0.3 mixture gave the antibiotic Y, elution with a 89.5:10:0.5 mixture gave the antibiotic X, followed by the antibiotic W, the elution of which was achieved using a 300:55.6 mixture. The fractions containing pure components were concentrated to small volumes, diluted with water, adjusted to pH 8.5 to 9.0 and then extracted with chloroform. After washing with water, the organic extracts were dried on sodium sulfate, and then concentrated to a small volume.

Addition of an equivalent of methanolic hydrogen chloride gave substantially pure hydrochlorides of antibiotic Z (0.04 g), antibiotic Y (0.2 g), antibiotic X (0.02 g) and antibiotic W (0.03 g) as microcrystalline powders. Recrystallization of antibiotics W, Y and Z from methanol:n-butanol gave the corresponding pure hydrochlorides as yellow orange crystals, m.p. 208° to 210° C. (with decomposition) for antibiotics W, m.p. 195° to 196° C. (with decomposition) for antibiotic Y and m.p. 200° to 201° C. (with decomposition) for antibiotic Z.

EXAMPLE 6

Purification of Antibiotic Y

A 20 mg sample of antibiotic Y was dissolved in 1 ml of 0.2 N aqueous hydrochloric acid and the solution was heated for 25 minutes at 90°. A crystalline yellow orange precipitate was collected by filtration after cooling, then washed with water and dried over phosphorus pentoxide overnight under vacuum. 10 mg of the aglycone of antibiotic Y were thus obtained in pure form, m.p. 168° C., m/e 368 (M+). After the precipitation of the aglycone, the almost colorless aqueous acidic solution contained a compound which reduced Fehling's solution and gave a positive reaction with ninhydrin. By paper and thin layer chromatography the compound was indistinguishable from an authentic sample of daunosamine (3-amino-2,3,6-trideoxy-L-lyxo-hexose), the amino sugar component of daunorubicin and doxorubicin.

We claim:

1. A biologically pure culture of the microorganism *Streptomyces peucetius* var. *aureus* ATCC 31428, said culture being capable of producing 11-deoxy-14-hydroxy-carminomycin, 11-deoxy-carminomycin and 11-deoxy-13-deoxo-carminomycin in recoverable quantities upon fermentation in an aqueous nutrient medium containing assimilable sources of carbon, nitrogen and inorganic substances.

2. A process for producing an antibiotic complex including a mixture of the compounds having the formula:

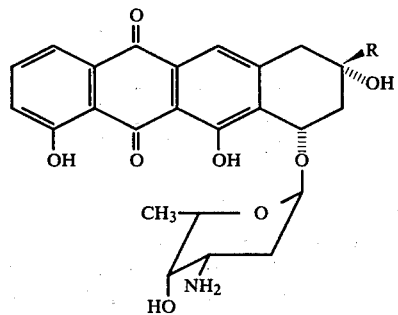

wherein R is $CO-CH_2-OH$, $COCH_3$, or $CH_2-CH_3$ and a salt thereof, said process comprising cultivating the microorganism *Streptomyces peucetius* var. *aureus* ATCC 31428, under aerobic conditions in an aqueous culture medium containing an assimilable source of carbon, an assimilable source of nitrogen and mineral salts and recovering said antibiotic complex from the culture medium.

3. A process according to claim 2 wherein said cultivating is carried out for 3 to 7 days, at a temperature of from 25° C. to 37° C. and at a pH which is initially from 6.5 to 7.0 and which is from 6.5 to 8.0 at the end of the cultivating step.

4. A process according to claim 2, further comprising separating mycelium from the culture medium by filtration at pH 4 with the aid of diatomaceous earth, extracting the filter cake with a water soluble solvent, combining the concentrated extracts with the filter culture medium, adjusting the pH to 8.5–9.0, re-extracting the antibiotic complex with a water immiscible organic solvent, concentrating said re-extracted antibiotics under reduced pressure and precipitating a crude antibiotic complex by adding n-hexane to said concentrated re-extracted antibiotic complex.

5. A process according to claim 2 further comprising isolating from the antibiotic complex 11-deoxy-14-hydroxy-carminomycin, 11-deoxy-carminomycin or 11-deoxy-13-deoxo-carminomycin.

6. A process according to claim 5 wherein said isolating is effected by silica gel column chromatography.

* * * * *